United States Patent [19]

Maeda

[11] Patent Number: 5,266,314
[45] Date of Patent: Nov. 30, 1993

[54] INSECTICIDE MAKING USE OF VIRUSES AND PREPARATION PROCESS THEREOF

[76] Inventor: Susumu Maeda, RC2-103, 110, Nishi 4-chome, Koyamacho, Tottori-shi, Tottori-ken, Japan

[21] Appl. No.: 752,217

[22] Filed: Aug. 21, 1991

Related U.S. Application Data

[63] Continuation of Ser. No. 341,283, Apr. 21, 1989, abandoned, which is a continuation of Ser. No. 937,058, Dec. 2, 1986, abandoned.

[30] Foreign Application Priority Data

Dec. 2, 1985 [JP] Japan ................... 60-271154

[51] Int. Cl.$^5$ ............ A01N 63/00; C12N 7/01; C12N 15/87
[52] U.S. Cl. ............... 424/93 A; 435/172.3; 435/235.1; 935/64
[58] Field of Search ......... 424/93, 93 A, 93 R, 424/93 T; 435/235.1, 172.3, 240.2, 320.1, 948; 935/64

[56] References Cited

U.S. PATENT DOCUMENTS

| | | | |
|---|---|---|---|
| 4,745,051 | 5/1988 | Smith | 435/69.1 |
| 4,762,785 | 8/1988 | Comai | 435/172.3 |
| 5,004,687 | 4/1991 | Miller | 435/69.1 |

OTHER PUBLICATIONS

Kondo, A. et al. 1991 *J. Virology* vol. 65 pp. 3625–3632.
Comptes Rendus Acad. Scid., vol. 290, pp. 579–582, Feb. 25, 1980, G. Croizier, et al., "Virologie-Selection De Types Viraux Les Infections Doubles A Baculovirus Chez Les Larves De Lepidoptere".
Journal of Virology, vol. 34, No. 3, pp. 693–703, Jun. 1980, M. D. Summers, et al., "Physical Maps Of Autographa Californica And Rachiplusia Ou Nuclear Polyhedrosis Virus Recombinants".
Lee, H. H. et al. 1979, *Journal of Virology* vol. 31 pp. 240–252.
Miller, L. K. 1981. *Journal of Virology* vol. 39 pp. 973–976.
Tsichlis, P. N. et al. 1980, *Journal of Virology* vol. 33 pp. 238–249.
Tsichlis, P. N. et al. 1980, *Proc. Nat. Acad. Sci. USA* vol. 77 pp. 536–540.
Ramakrishnan N. 1976 Proc. Natl. Acad. Sci. India 46(B) I & II 110–116.
Chelliah S. et al 1984 Integrated Pest & Disease Management National Seminar. Sep. 1984, pp. 139–149.
Merdan A. et al 1977. Entomophaga 22 (4) 413–420.
Luthy P. et al 1985 BioEssays 2 (1) 22–25 Designing Mircoorganisms for Insect Control.
Smith G. E. et al 1983 Molec. Cell Biol. 3 (12) 2156–2165.
Okada M. 1977 Review of Plant Protection Research 10:102–28.
Kinzer et al 1976 J. Econ. Eatomol 69 (5) 697–701.

*Primary Examiner*—Richard A. Schwartz
*Assistant Examiner*—Mary E. Mosher
*Attorney, Agent, or Firm*—Oblon, Spivak, McClelland, Maier & Neustadt

[57] ABSTRACT

A composition comprising a hybrid nuclear polyhedrosis virus capable of destroying two species of insects and a method for obtaining the virus by infecting a mixture of two virus strains and successively culturing in two insect cell lines.

4 Claims, No Drawings

INSECTICIDE MAKING USE OF VIRUSES AND PREPARATION PROCESS THEREOF

This application is a continuation of application Ser. No. 07/341,238 filed on Apr. 21, 1989, now abandoned, which is a continuation of Ser. No. 06/937,058, filed on Dec. 2, 1986, now abandoned.

BACKGROUND OF THE INVENTION

1) Field of the Invention

This invention relates to a so-called viral insecticide which is effective in destroying or controlling injurious insects by using microorganisms pathogenic to them, and to a preparation process thereof.

2) Description of the Prior Art

Viral insecticides adapted to perform bacterial destruction or control of injurious insects by using microorganisms pathogenic to them are attracting interests in recent years, because the microbial insecticides do not give chemical injury to plants and animals. Among such microbial insecticides, certain virus preparations containing nuclear polyhedrosis virus (hereinafter abbreviated as "NPV") as active ingredients have already been put on the market in the United States. The recent state of art of bacterial insecticides was reported for example by Ayusawa, Fujiyoshi, et al. in "Hakko Kogaku", 51, 351-365 (1973). Kamizumi and Katagiri reported separately the utilization of bacterial insecticides in "Hakko Kogaku", 51, 365-374 (1973).

Conventional virus preparations however encounter difficulties in their mass production and have hence poor utility in view of their production costs, since they are each prepared by feeding an artificial feed, which has been added with NPV of a specific host insect, to larvae of the insect so as to infect the NPV to the larvae, allowing both larvae and NPV to multiply as a result of the feeding of the artificial feed, collecting remains of diseased insects, grinding them, and then forming the resultant powder as a preparation.

Since the host range of insect viruses is generally specified to limited species of insects, there is another problem that it is impossible to obtain any single virus preparation capable of showing insecticidal effects against a wide variety of insects.

It is therefore essential to overcome the above-mentioned problems in order to use a virus preparation actually as an agricultural chemical for destroying or controlling injurious insects.

SUMMARY OF THE INVENTION

With the foregoing in view, the present invention has as one object the provision of a virus preparation capable of destroying or controlling two species of injurious insects at the same time by forming a recombinant virus (a hybrid of two viruses of different species) using established insect cell lines to obtain a virus capable of showing different host specificity.

Another object of this invention is provide a process for the preparation of the recombinant virus, the active ingredient of the above-described virus preparation, which process can also be carried out by a mass production method using a silkworm, *Bombyx mori,* by a method similar to those conducted in sericulture.

In one aspect of this invention, there is thus provided an insecticide comprising, as an active ingredient, a recombinant virus obtained by infecting a mixture of both strains of two nuclear polyhedrosis viruses, the host insects of which are different from each other, to two types of cells successively, one of said two types of cells permitting multiplication of only one of the two nuclear polyhedrosis viruses and the other allowing multiplication of the other nuclear polyhedrosis virus only.

In another aspect of this invention, there is also provided a process for the preparation of an insecticide, which comprises infecting a mixture of both strains of two nuclear polyhedrosis viruses, the host insects of which are different from each other, to a first type of cells in which only one of the viruses is allowed to multiply, culturing the thus-infected first type o cells, collecting the supernatant of the resultant culture mixture, infecting the viruses in the supernatant to a second type of cells in which the other virus is solely allowed to multiply, culturing the thus-infected second type of cells, collecting the supernatant of the resultant culture mixture, infecting the viruses in the supernatant again to a monolayer supply of the first type of cells, and then cloning the resultant mixture by a plaque assay to obtain a recombinant virus consisting of a genetically uniform virus strain, and then forming the recombinant virus, either as is or after infecting same to silkworm larvae and multiplying same therein, as an active ingredient into a preparation.

DETAILED DESCRIPTION OF THE INVENTION

In order to facilitate the understanding of the insecticide and its preparation process to both of which the present invention is directed, a description will hereinafter be made of one example in which an NPV using both of the silkworm, *Bombyx mori,* and a tobacco cutworm, *Spodoptera litura* as host insects is employed. Namely, a recombinant virus is formed in the following procedure by using the NPV T3 strain of the silkworm and the NPV OT 102 strain of the tobacco cutworm as two species of NPVs and BmN cells derived from the silkworm and CLS79 cells or SF21E cells derived from a related species of the tobacco cutworm as cells derived from the host cells.

First of all, a mixture of the NPV T3 strain of silkworm and NPV OT 102 strain of the tobacco cutworm is infected to the CLS 77 cells or SF21E cells. This infection may preferably be carried out at a rate of 5 virus particles per cell (m.o.i. 5). The thus-infected cells are then cultured for 2–3 days. The cell fluid of the culture is collected and thereafter infected to the BmN cells derived from the silkworm. After the infection, the cells are inoculated on a culture medium and then cultured for 3 days.

After the culture, the supernatant of the culture mixture is collected and infected again to a monolayer of CLS79 cells or SF21AE cells.

The thus-infected cells contain two types of species of viruses together, one being capable of forming polyhedral inclusion bodies and the other being practically incapable of forming any inclusion body. A recombinant virus which does not form any polyhedral inclusion body and has genetic uniformity can be obtained by cloning a virus of the latter type selectively by a plaque assay.

When the above-formed recombinant virus was infected to BmN cells derived from the silkworm, it underwent multiplication there. It has hence been confirmed that the strain of the recombinant virus can multiply in both CLS79 cells or SF21AE cells derived from the related species of the tobacco cutworm and BmN cells derived from the silkworm.

For mass production of the recombinant virus as an insecticide formed in the above manner, larvae of the silkworm, which has been improved as a domestic animal in sericulture for several thousand years, can be used at a low cost.

Incidentally, the recombinant virus of this invention was multiplied in BmN or SF21AE cells and viral DNA was extracted from the resultant viral particles. DNA fragments which had been obtained by treating the DNA with restriction enzymes were investigated by agarose-gel electrophoresis and DNA hybridization. As a result, the virus was found to contain a part of the DNAs of both of the two species of the NPV T3 (a strain of the silkworm) and the NPV OT 102 (a strain of the tobacco cutworm) and hence to be a recombinant virus of both viruses.

By combining two species of NPVs, the host insects of which are different from each other, using the above-mentioned genetic technique, it is possible to form a recombinant virus capable of infecting both of the host insects and multiplying therein as described above. The present invention has hence opened the door to provide in a large volume a virus preparation at a low cost, which is useful in destroying or controlling a wide variety of injurious insects, by forming a recombinant virus from two species of NPVs the host insects of which are different from each other, infecting the recombinant virus to silkworm larvae and allowing it to multiply there, and then forming the thus-multiplied recombinant virus into a preparation.

For example, a virus preparation which can destroy or control both of a white butterfly, *Pieris rapae,* an insect injurious to cabbage, and a diamond back moth, *Plutella xylostella* can be prepared by forming a recombinant virus from a virus infectious to *Pieris rapae* and another virus infectious to *Plutella xylostella* and then using the recombinant virus as an active ingredient.

Since the present invention can form a recombinant virus practically incapable of forming any syncytium as described above, the present invention has a merit that an insecticidally-active ingredient free of persistent toxicity can be provided by infecting the recombinant virus to silkworm larvae and then culturing it on a large scale. Namely, the recombinant virus substantially incapable of forming any polyhedral inclusion body is embedded in inclusion bodies of NPV of the silkworm when the recombinant virus is infected to and multiplied in silkworm larvae together with NPV of the silkworm. Therefore, the resulting insecticide remains stable for the period until the insecticide is sprayed in the field. When it is sprayed, the recombinant virus is released from its embedded state and can no longer survive for any long period of time, thereby solving the problem of persistent toxicity.

The preparation of the insecticide of this invention may be effected preferably in the following manner. After confirming the safety of the recombinant virus formed in the above-described manner to small animals, an extender such as bentonite, kaolin or talc the particle size of which is generally about 200 mesh or so is added. One or more substances capable of enhancing the insecticidal activities may also be added in small amounts as needed. The resultant mixture is then formed into a preparation.

Although the recombinant virus, the active ingredient of the insecticide of this invention, was not formed by techniques of genetic engineering like a so-called recombinant DNA experiment, the resulting viruses are considered to be safer insecticides. It is expected that the above-mentioned recombinant viruses can be made by a genetic technique such as that routinely used in recombinant DNA experiments.

The present invention and its advantageous effects will hereinafter be described specifically by the following examples.

EXAMPLE 1

Established cells of CLS79 cells (of a species related to the tobacco cutworm, *Spodoptera litura*) were cultured as a monolayer at 27° C. in a petri dish of 60 mm across until the number of cells reached $1.5 \times 10^6$ cells/petri dish. After the culture, the culture medium was removed from the petri dish. A mixture of the BmNPV NPV T3 strain and the SNPV NPV OT 102 strain was infected in the below-described manner to the cells left over in the petri dish. First of all, about 0.1 ml of a virus solution was prepared to contain about 5 PFUs (plaque forming units) per cell (about 5 m.o.i.). The virus solution was added to each cell in the petri dish and the resultant mixture was allowed to stand for 1 hour to infect the virus to the cells. During this period of time, the petri dish was tilted from time to time.

After completion of the above infecting treatment, the virus solution was removed from the petri dish and the cells still remaining in the petri dish were washed three times with IPL-41 liquid culture medium so as to remove unadsorbed virus from the petri dish.

Thereafter, 4.5 ml of a liquid culture medium containing 10% fetal calf serum was added to the cells in the petri dish. The cells were cultured at 27° C. The supernatant of the culture mixture was sampled respectively 24 hours and 40 hours later. The thus-obtained supernatant samples were each diluted to 10–1000 times, whereby various virus solutions having different virus concentrations were obtained. By using each of the thus-diluted solutions separately, the virus in the diluted solution was infected to BmN established cells derived from the silkworm, followed by culture of the thus-infected cells for 2–3 days. After completion of the culture, the supernatant of each culture mixture was collected and the virus contained in the supernatant was again infected to CLS79 cells, Cloning was then conducted by a plaque assay to form a recombinant virus.

Each of the thus-obtained clone strains was infected separately to both BmN cells and CLS79 cells. Cultures of the cell lines identified below were deposited under the provision of the Budapest Treaty with the American Type Culture Collection, 12301 Parklawn Drive, Rockville, Maryland 20852, U.S.A. The cultures can be accessed under the stated identified numbers.

| MICROORGANISM | ATCC |
|---|---|
| Cell line CLS 79 | CRL 9373 deposited December 2, 1986 |
| Cell line SF 21 AE | CRL 937 deposited December 2, 1986 |
| Cell line BmN | CRL 10889 deposited September 26, 1991 |

A clone strain capable of undergoing multiplication in both cells was selected and employed as an insecticidally active ingredient. By the way, the thus-obtained virus can be infected to silkworm larvae for its mass multiplication.

Formation of the recombinant virus into a preparation

The recombinant virus formed in the above-described manner was orally infected to third-instar silkworms and at the end of fifth instar, those perished with one or more diseases were collected. A buffer was added to the thus-collected remains and the resultant mixture was ground, followed by centrifugation at 3000 r.p.m for 10 minutes. The resultant precipitate was separated and collected. The thus-obtained precipitate was formed into powder by a method known per se in the art, thereby obtaining an insecticide.

Insecticidal Test

The above-obtained preparation was added at a dilution of 1/1000 to an artificial feed for tobacco cutworms, *Spodoptera mori*. After feeding the artificial feed, the tobacco cutworms were allowed to grow to investigate their infection by NPV. It was confirmed that 100% of the tobacco cutworms were infected and perished in two weeks.

EXAMPLE 2

A recombinant virus was formed in the same manner as in Example 1 except that established cells of SF21AE cells were used instead of the established cells of CLS79 cells and the cell concentration in a petri dish was adjusted to $1.0 \times 10^6$ cells/petri dish.

The thus-obtained recombinant virus was able to undergo multiplication in both SF21AE cells and BmN cells.

The recombinant virus was formed into a preparation in the same manner as in Example 1, thereby obtaining an insecticide.

Using the above-obtained insecticide, an insecticidal test was conducted under the same conditions as in Example 1. Similar to Example 1, it was confirmed that 100% of the tobacco cutworms were infected and perished in two weeks.

What is claimed is:

1. A composition comprising a hybrid nuclear polyhedrosis virus capable of infecting and multiplying in both BMN and in either CLS79 or SF21AE cells, obtained by the steps:
   a) infecting a first cell strain selected from the group consisting of CLS79 and SF21AE cells with a mixture of a first and a second strain of nuclear polyhedrosis virus wherein said first cell strain permits replication of only the first viral strain but not replication of the second viral strain;
   b) culturing the infected first cell strain;
   c) infecting a second cell strain consisting of BmN cells derived from *Bombyx mori* with cell fluid derived from the infected first cell strain wherein said second cell strain permits replication of only the second viral strain but not replication of the first viral strain;
   d) culturing the infected second cell strain;
   e) collecting said hybrid virus.

2. The composition of claim 1 wherein step c) comprises: infecting a second cell strain with the supernatant fluid obtained from the infected first cell strain.

3. A process for preparing an insecticidal composition which comprises the steps:
   a) infecting a first cell strain selected from the group consisting of CLS79 and SF21AE cells with a mixture of a first and a second strain of nuclear polyhedrosis virus wherein said first cell strain permits replication of only the first viral strain but not replication of the second viral strain;
   b) culturing the infected first cell strain;
   c) infecting a second cell strain consisting of BmN cells derived from *Bombyx mori* with the supernatant fluid obtained from the infected first cell strain;
   d) culturing the infected second cell strain;
   e) infecting a fresh supply of the first cell strain with the supernatant fluid obtained from the infected second cell strain thereby identifying the cells containing a hybrid virus capable of replicating in both said first and second cell strains;
   f) collecting a hybrid virus then forming the recombinant virus as an active ingredient into a preparation.

4. The process of claim 3 which further comprises the step: infecting silkworm larvae with the hybrid virus and replicating said hybrid virus therein.

* * * * *